United States Patent [19]

Morrison, Jr. et al.

[11] 4,288,365
[45] Sep. 8, 1981

[54] PYRIDO DERIVATIVES

[75] Inventors: Robert W. Morrison, Jr.; William R. Mallory; Virgil L. Styles, all of Raleigh, N.C.

[73] Assignee: Burroughs Wellcome Co., Research Triangle Park, N.C.

[21] Appl. No.: 76,406

[22] Filed: Sep. 17, 1979

Related U.S. Application Data

[62] Division of Ser. No. 926,072, Jul. 19, 1978, abandoned.

[30] Foreign Application Priority Data

Jul. 20, 1977 [GB] United Kingdom ............... 30380/77

[51] Int. Cl.³ .................. C07D 487/04; A61K 31/505
[52] U.S. Cl. ................... 260/243.3; 544/256; 544/320; 544/321; 544/279; 544/262; 544/236
[58] Field of Search ...................... 544/256; 260/243.3

[56] References Cited

U.S. PATENT DOCUMENTS 3,947,442 3/1976 Beckwith et al. ................... 544/236

FOREIGN PATENT DOCUMENTS 0000383 1/1979 European Pat. Off. ............ 544/256
447094 5/1957 United Kingdom .
774095 5/1957 United Kingdom .
798646 7/1958 United Kingdom .
1129084 10/1968 United Kingdom .
1427508 3/1976 United Kingdom .

OTHER PUBLICATIONS

Morrison et al., *Organic Chemistry.*
Hirano et al., "Chemical Abstracts", vol. 52, 1958, Col. 3838e.
"Chemical Abstracts", vol. 84, 1976, Col. 59531m.

Primary Examiner—Donald G. Daus
Assistant Examiner—James H. Turnipseed
Attorney, Agent, or Firm—Donald Brown

[57] ABSTRACT

Compounds of the general formula (I)

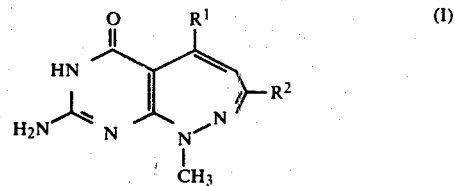

wherein $R^1$ and $R^2$ are selected from a lower alkyl group, a phenyl group (optionally substituted by one or more hydroxy or lower alkoxy groups), a pyridyl group or a group —$CO_2R$ where R is a lower alkyl group, (provided that when $R^1$ is a group —$CO_2R$, $R^2$ is a lower alkyl group) are disclosed.

The compounds of formula (I) are useful as intermediates to compounds of other ring systems which are of pharmacological interest.

Certain of the compounds of formula (I) are also useful as antimicrobial agents.

6 Claims, No Drawings

PYRIDO DERIVATIVES

This is a division of application Ser. No. 926,072, filed July 19, 1978, now abandoned.

This invention relates to 1H-pyrimido{4,5-c}-1,2-diazepines, methods of their preparation, compositions and formulations containing them and their uses as antimicrobial agents, and as intermediates for heterocyclic transformations.

The present invention provides novel 1H-pyrimido {4,5-c}-1,2-diazepines of formula (I), or their tautomers, or salts thereof,

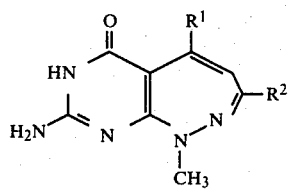

wherein $R^1$ and $R^2$ are the same or different and are selected from a lower alkyl group, a phenyl group (optionally substituted by one or more hydroxy or lower alkoxy groups), a pyridyl group or a group $CO_2R$ in which R is a lower alkyl group; provided that when $R^1$ is a group $CO_2R$ then $R^2$ may only be a lower alkyl group.

The term "lower" as used herein in conjunction with an alkyl or alkoxy group is indicative of the fact that such groups have from 1 to 4 carbon atoms arranged in a straight or branched chain.

It is to be understood that compounds where tautomerism is possible between, on the one hand, a hydroxy group and an oxo group, and on the other hand, an amino group and an imino group, at a particular position on the (1H)-pyrimido {4,5-c}-1,2-diazepines of formula (I), the more stable forms are respectively, the oxo group and the amino group. The formulae used in the present specification show the more stable form of such compounds.

It should be noted that the compounds of formula (I) possess a completely new type of skeletal ring structure, that is, the pyrimido {4,5-c}-1,2-diazepine bicyclic rings. Accordingly, an important advantage of the present invention is that a whole new area of novel chemistry has been opened up for further investigation by the provision herein of processes enabling the production of compounds of formula (I).

The above compounds of formula (I) have been found to be particularly susceptible to ring-opening and ring-closure rearrangement reactions. Depending upon the nature of the substituents, their location, and reaction conditions, the compounds of the present invention may be converted to either pyrido {2,3-d}-pyrimidines, pyrimido {4,5-c}pyridazines, or pyrazolo {2,3-d}pyrimidines which compounds may then be converted by reactions well known in the art, for example hydrolysis, halogenation, amination, reduction, oxidation, nucleophilic substitution, electrophilic substitution and elimination, to compounds with the same basic skeletal ring structure but different substituents which compounds have biological activity. For example, the pyrido {2,3-d}-pyrimidines of U.K. Patent Specification Nos. 774,094 and 774,095 have activity against lactic acid bacteria, the pyrido {2,3-d}pyrimidines of U.K. Patent Specification No. 1,129,084 are useful as diuretics, the pyrido {2,3-d}pyrimidines of U.K. Patent Specification No. 1,427,508 are active against micro-organisms which utilise the de novo synthesis of riboflavin and, the pyrazolo {2,3-d}pyrimidines of U.K. Patent Specification No. 798,646 are active as antimetabolites in purine synthesis. The compounds of the present invention may therefore be used as intermediates for the production of pharmaceuticals which have one of the above three specified ring structures.

Within the class of (1H)-pyrimido {4,5-c}-1,2-diazepines of formula (I) there is a group of compounds represented by formula (II):

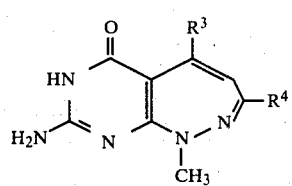

wherein $R^3$ is a phenyl group optionally substituted with one or more hydroxy groups; and $R^4$ is a group $CO_2R$ in which R is as hereinbefore defined, which exhibit dihydropteroic acid biosynthesis inhibitory activity.

Thus, the above compounds of formula (II) inhibit one of the enzymes, namely dihydropteroate synthetase, which enables micro-organisms to synthesise an essential intermediate in the production of tetrahydrofolate co-factors. Most of these co-factors are one-carbon adducts of tetrahydrofolic acid and they are essential metabolites in cells for the biosynthesis of purines, thymidylic acid, serine and several other biologically important compounds. Man and other higher animals are unable to synthesise folic acid and therefore they have to obtain it from food which contains the required preformed folates.

On the other hand, most micro-organisms synthesise folic acid from simpler chemicals. Generally the biosynthetic process first provides 'dihydropteridine' (Pt), i.e. 2-amino-4-hydroxy-6-hydroxymethyl-7,8-dihydropteridine (HMPt) pyrophosphate ester, from its immediate precursor HMPt in the presence of the enzyme hydroxymethyldihydropteridine pyrophosphokinase (HMPPS). Pt then condenses with p-aminobenzoic acid (pAB) in the presence of the enzyme dihydropteroate synthetase to form dihydropteroic acid (DPtA). This intermediate further condenses with a glutamate to form dihydrofolic acid (DFA or 'folate') which is then enzymatically reduced to produce the essential tetrahydrofolate.

As examples of compounds which are particularly active and fall within this class are 8-amino-3-carbethoxy-1-methyl-5-phenyl-1H-pyrimido {4,5-c}-1,2-diazepin-6(7H)-one and 8-amino-3-carbomethoxy-1-methyl-5-(3-hydroxyphenyl)-1H-pyrimido {4,5-c}-1,2-diazepin-6(7H)-one. These compounds additionally have the ability to potentiate the antimicrobial activity of a 2,4-diamino-5-benzyl pyrimidine and/or a sulphonamide, for example trimethoprim or sulphamethoxazole.

Also within the class of (1H)-pyrimido {4,5-c}-1,2-diazepines of formula (III):

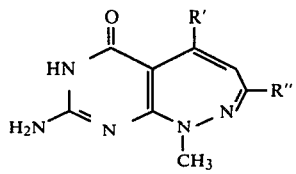

(III)

wherein R' is a phenyl group optionally substituted with one or more lower alkoxy groups and R" is a group —$CO_2R$ in which R is as hereinbefore defined, or a phenyl group which have anti-protozoal, for example anti-coccidial, activity.

As examples of compounds falling within formula (III) and of particular interest are 8-amino-3-carbomethoxy-1-methyl-5-(3,4,5-trimethoxyphenyl)-1H-pyrimido {4,5-c}-1,2-diazepin-6(7H)-one; 8-amino-3-carbethoxy-1-methyl-5-(2,4-dimethoxyphenyl)-1H-pyrimido {4,5-c}-1,2-diazepin-6(7H)-one and 8-amino-3,5-diphenyl-1-methyl-1H-pyrimido {4,5-c}-1,2-diazepin-6(7H)-one. Such compounds alternatively have the ability to potentiate the antimicrobial activity of combinations of a 2,4-diamino-5-benzylpyrimidine and a sulphonamide. Thus compounds of formula (III) may for example, potentiate the antiprotozoal activity of a mixture of diaveridine and sulphaquinoxaline.

The compounds of formula (I) may be prepared by the reaction of 6-(1-methylhydrazine)isocytosine, represented by formula (IV):

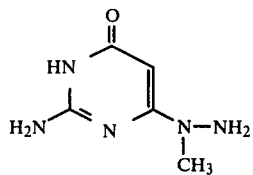

(IV)

with an α,γ-dicarbonyl compound of formula (V):

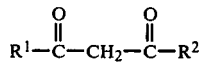

(V)

wherein $R^1$ and $R^2$ are as hereinbefore defined.

The preparation is suitably achieved by refluxing in a suitable solvent, most desirably a hydroxylic solvent such as a $C_1$–$C_4$ alkanol, glacial acetic and/or water, at a reflux temperature for up to several days. Optimally the reaction is carried out in refluxing methanol.

In the preparation of compounds of formula (I) some other bicyclic compound may be formed as a byproduct. In such instances it may be necessary to isolate the required compound by the usual procedures known in the art.

The reaction of the compound of formula (IV) with those of formula (V) is a two-step process, the first step being a condensation reaction and the second step a cyclisation of the so formed intermediate. It is believed that the intermediate formed has the formula (IV):

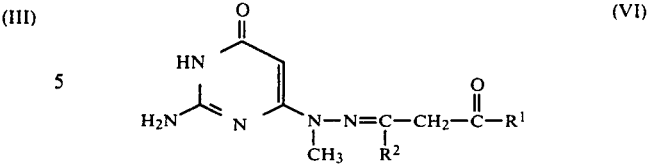

(VI)

wherein $R^1$ and $R^2$ are as hereinbefore defined. The compounds of formula (VI) are novel compounds which form a further aspect of the invention. It is to be understood that the compounds of formula (VI) may either be converted in situ to compounds of formula (I) by continuing the reaction to completion under the original conditions or alternatively may be isolated and then converted to compounds of formula (I) under the reaction conditions suitable for the direct conversion of the intermediate to compounds of formula (I).

The type of dicarbonyl compound of formula (V) used in the preparation of compounds of formula (I) will of course depend upon the substituents $R^1$ and $R^2$ in the compounds of formula (I).

Thus when $R^1$ is either a phenyl group (optionally substituted with one or more hydroxy or lower alkoxy groups) or a pyridyl group and $R^2$ is a group $CO_2R$ in which R is a lower alkyl group, viz a compound of formula (VII):

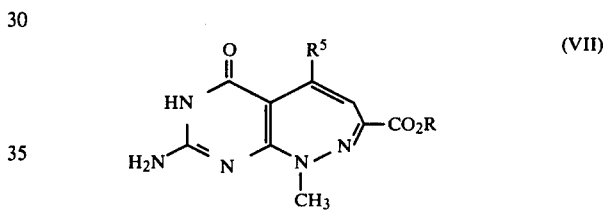

(VII)

where R is as defined above and $R^5$ is a phenyl group (optionally substituted with one or more hydroxy or lower alkoxy groups) or a pyridyl group, the dicarbonyl compound will be an α,γ-diketoester of formula (VIII):

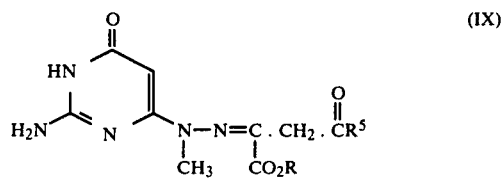

(VIII)

where R and $R^5$ are as defined hereinabove. In this case the believed intermediate is a compound of formula (IX):

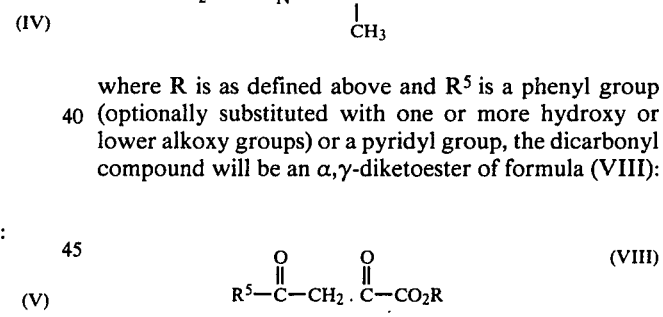

(IX)

where R and $R^5$ are as defined hereinabove. Compounds of formula (IX) are novel and form a further aspect of the invention.

When in the compounds of formula (I), $R^1$ and $R^2$ are the same and are both a lower alkyl group, a phenyl group (optionally substituted with one or more hydroxy or lower alkoxy groups) or a pyridyl group, viz a compound of formula (X):

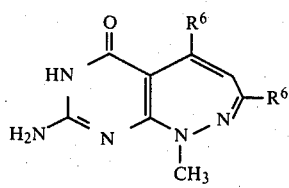
(X)

where $R^6$ is a lower alkyl group, a phenyl group (optionally substituted with one or more hydroxy or lower alkoxy groups) or a pyridyl group, then the dicarbonyl compound will be a symmetrical 1,3-diketone of formula (XI):

$$R^6-CO.CH_2.CO.R^6 \quad (XI)$$

where $R^6$ is as defined above. In this case the intermediate will be a compound of formula (XII):

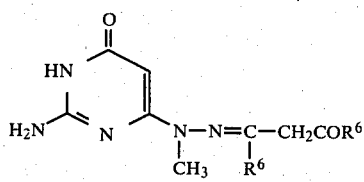
(XII)

where $R^6$ is as defined above. Compounds of formula (XII) are novel and form a further aspect of the present invention.

When, in the compounds of formula (I), $R^1$ is a lower alkyl group and $R^2$ is a group $CO_2R$ in which R is a lower alkyl group, viz a compound of formula (XIIIa):

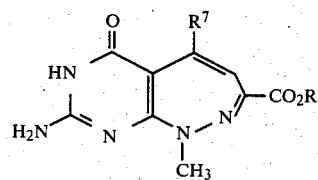
(XIII)

where R is as hereinbefore defined and $R^7$ is a lower alkyl group or, alternatively $R^1$ is a group $CO_2R$ where R is a lower alkyl group and $R^2$ is a lower alkyl group, viz a compound of formula (XIIIb):

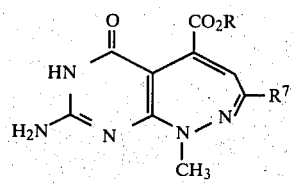
(XIIIb)

when R and $R^7$ are as defined above, the the diketo compound will be an α,γ-diketo ester of formula (XIV):

$$R^7COCH_2.COCO_2R \quad (XIV)$$

where R and $R^7$ are as defined above. The reaction of a compound of formula (XIV) with the compound of formula (IV) always leads to a mixture of condensation products, believed to be compounds of formula (XV):

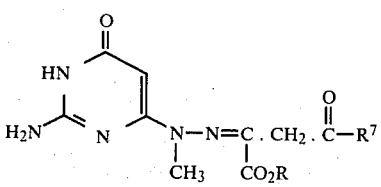
(XV)

where R and $R^7$ are as hereinbefore defined and formula (XVI):

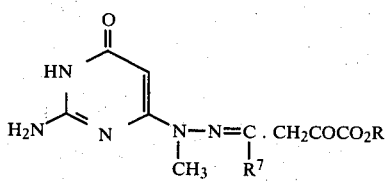
(XVI)

where R and $R^7$ are as hereinbefore defined.

The compounds of formulae (XV) and (XVI) may either be separated from each other, for example by column chromatography before conversion into compounds of formulae (XIIIa) and (XIIIb) respectively, or preferably they may be cyclised together and the so produced isomeric compounds (XIIIa) and (XIIIb) may be separated from each other by methods known in the art for separating isomeric compounds, for example by column chromatography on, for instance, silica gel.

The compounds of formulae (XV) and (XVI) are novel compounds which form further aspects of the present invention.

Compounds of formula (I) wherein $R^1$ is a lower alkyl group, a phenyl group (optionally substituted with one or more hydroxy or lower alkoxy groups) or a pyridyl group and $R^2$ is a group $CO_2R$ in which R is as hereinbefore defined may be converted to pyrido {2,3-d}pyrimidines by saponification at room temperature followed by acidification to pH 2.0 to 5.0 to yield the carboxylic acid corresponding to the starting ester and subsequent heating to 100° to 150° C. in an alkyl cellosolve or in dimethyl sulphoxide. Thus according to a further aspect of the present invention there is provided a method of making a compound of formula (XVIIa):

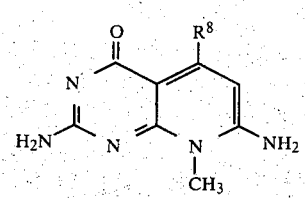
(XVII)

where $R^8$ is a lower alkyl group, a phenyl group (optionally substituted with one or more hydroxy or lower alkoxy groups) or a pyridyl group which comprises heating in an alkyl cellosolve or in dimethyl sulphoxide, a compound of formula (XVIII):

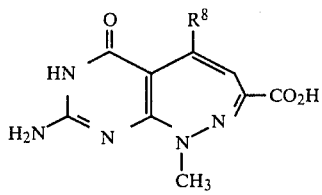

wherein R[8] is as hereinbefore defined.

The compounds of formulae (XVII) and (XVIII) are novel and constitute further aspects of the present invention.

The saponification of a compound of formula (I) wherein R[1] is a lower alkyl group, a phenyl group (optionally substituted with one or more hydroxy or lower alkoxy groups) or, pyridyl group and R[2] is a group $CO_2R$ in which R is as hereinbefore defined may conveniently be carried out using an aqueous alkali, for example aqueous sodium hydroxide. The subsequent acidification step which produces the corresponding compound of formula (XVIII) is conveniently performed using an aqueous acid, preferably an aqueous inorganic acid, for example hydrochloric acid.

The alkyl cellosolve in which compounds of formula (XVIII) may be heated to produce compounds of formula (XVII) is preferably methyl cellosolve, and the heating should be carried out for 2-3 hours at 100° to 150° C., most preferably at 125° C. Preferably the compound of formula (XVIII) is separated from the reaction medium in which it is produced before it is heated to produce ring rearrangement.

Compounds of formula (I) wherein (a) R[1] is a lower alkyl group, a phenyl group (optionally substituted with one or more hydroxy or lower alkoxy groups) or a pyridyl group and R[2] is a group $CO_2R$ in which R is a lower alkyl group; or (b) R[1] and R[2] are the same and each is a lower alkyl group, a phenyl group (optionally substituted with one or more hydroxy or lower alkoxy groups) or a pyridyl group may be converted to pyrazolo {3,4-d}pyrimidines by heating in aqueous acid at a temperature of greater than 70° C. Thus according to a further aspect of the present invention there is provided a process of making a compound of formula (XIX):

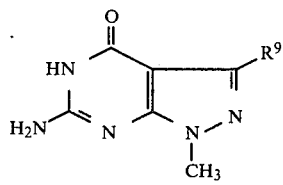

wherein R[9] is a lower alkyl group, a phenyl group (optionally substituted with one or more hydroxy or lower alkoxy groups) or a pyridyl group which comprises heating in aqueous acid a compound of formula (XX):

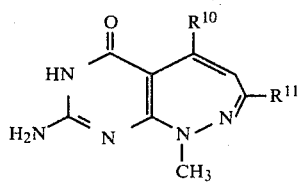

wherein (a) R[10] is a lower alkyl group, a phenyl group (optionally substituted with one or more hydroxy or lower alkoxy groups) or a pyridyl group and R[11] is a group $CO_2R$ in which R is as hereinbefore defined; or (b) R[10] and R[11] are the same and each is a lower alkyl group, a phenyl group (optionally substituted with one or more hydroxy or lower alkoxy groups) or, pyridyl group.

The acid for use in this reaction is conveniently an aqueous inorganic acid, for example hydrochloric acid, having a strength in the range of 0.5 to 2.0 M. Normally the reaction reaches completion after 2 or 3 hours.

The compounds of formula (XIX) are novel and constitute a further aspect of the present invention.

Compounds of formula (I) wherein R[2] is a lower alkyl group and R[1] is a group $CO_2R$ in which R is as hereinbefore defined may be converted to pyrimido {4,5-c}pyridazines by treatment with aqueous acid at room temperature. Thus according to yet a further aspect of the present invention there is provided a method of making a compound of formula (XXI):

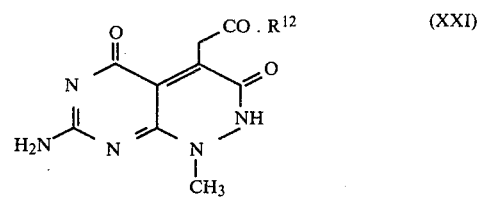

wherein R[12] is a lower alkyl group which comprises treating with aqueous acid at room temperature a compound of formula (XXII):

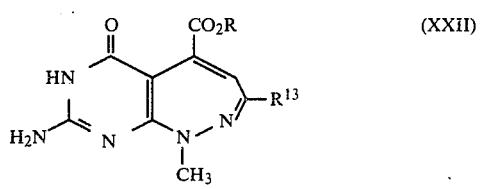

wherein R[13] is a lower alkyl group and R is as hereinbefore defined.

It should be noted that R[13] in formula (XXII) becomes R[12] in formula (XXI).

The conditions for this hydrolysis reaction should be mild i.e. carried out without heating, and the acid, which is preferably an inorganic aqueous acid, for example hydrochloric acid, should be added until the reaction medium reaches a pH of 3 or less. Normally the reaction is completed within 2 or 3 days.

The compounds of formula (XXI) are novel and constitute a further aspect of the present invention. The compounds of formula (XXI) may themselves be further converted to a different pyrimido {4,5-c}-pyridazine by boiling in a hydroxylic solvent, for example methyl cellosolve. Thus according to a further aspect of the present invention there is provided a method of making a compound of formula (XXIII):

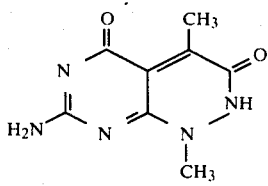 (XXIII)

which comprises heating a compound of formula (XXI) in boiling methyl cellosolve. Normally the heating is carried out for up to 24 hours.

The compound of formula (XXIII) is novel and constitutes a further aspect of the present invention.

It should be noted that regardless of the nature of 12 in the substituent at the 4-position in formula (XXI), cleavage normally results in the compound of formula (XXIII) which has a methyl group in its 4-position.

All the starting materials specified above for the various syntheses may be prepared by standard methods taught in the art.

As stated hereinabove the compounds of formula (II) or their tautomers, or salts thereof not only inhibit the growth of micro-organisms to some extent but also unexpectedly act with a potentiating effect when combined with a 2,4-diamino-5-benzylpyrimidine or with a sulphonamide, or with a combination of both these types of antimicrobial agents.

In a further aspect of the present invention therefore there is provided a composition for treating microbial infections, comprising an effective potentiating amount of a compound of formula (II) in combination with an effective amount of a 2,4-diamino-5-benzylpyrimidine, or a sulphonamide, or both.

The microbial infections against which the combinations of this invention are effective are protozoal or bacterial infections caused by those microorganisms which synthesise at least a substantial part of their tetrahydrofolate co-factor requirements. More specifically these infecting microorganisms are those which adequately absorb the pharmaceutical combinations disclosed herein and further are those in which these combinations have a synergistic effect in interfering with the de novo synthesis of the required tetrahydrofolate cofactors.

Also as stated hereinabove the compounds of formula (III), their tautomers and their salts not only inhibit the growth of protozoa but also unexpectedly act with a potentiating effect when combined with a combination of a 2,4-diamino-5-benzylpyrimidine and a sulphonamide.

In a further aspect the invention thus provides a composition for treating protozoal infections comprising an effective potentiating amount of a compound of formula (III) in combination with an effective amount of a combination of a 2,4-diamino-5-benzylpyrimidine and a sulphonamide.

In accordance with the above, the term "an effective amount" used in conjunction with the terms a 2,4-diamino-5-benzylpyrimidine and a sulphonamide means either (a) an amount of the 2,4-diamino-5-benzylpyrimidine or sulphonamide which is effective to a degree as an antimicrobial agent in its own right but which is potentiated by the use of a compound of formula (II), or its tautomer, or salt thereof or (b) an amount of the 2,4-diamino-5-benzylpyrimidine or sulphonamide which is ineffective as an antimicrobial agent but which when combined with a compound of formula (II), or its tautomer, or salt thereof, provides a composition which is an effective antimicrobial agent. An "effective potentiating amount" means an amount of the compound of formula (II), or formula (III), or its tautomer or salt thereof which increases the activity of a 2,4-diamino-5-benzylpyrimidine and/or a sulphonamide so as to provide a greater antimicrobial effectiveness for the whole combination.

The compounds of formula (II) or (III) either for use alone or in combination with a 2,4-diamino-5-benzylpyrimidine and/or a sulphonamide may be presented in association with a carrier in pharmaceutical formulations suitable for parenteral, topical, rectal or oral administration. The formulations for oral or rectal administration are advantageously presented in discrete units, such as tablets, capsules, cachets, ampoules or suppositories each containing a predetermined amount of compound, but may also be presented as a powder, as granules, as a solution or suspension in an aqueous or non-aqueous liquid, or as an ointment or paste for topical administration. For parenteral use, the formulations incorporating an aqueous or non-aqueous liquid carrier must be sterile and be presented in sealed containers. The formulations may be made by any of the known methods and may include one or more of the following accessory ingredients: diluents, solutes to render the solution isotonic with the blood, buffers, flavouring, binding, dispersing, surface-active, thickening, lubricating and coating materials, preservatives, bacteriostats, antioxidants, suppository and ointment bases, and any other acceptable excipients.

In another aspect of the present invention, therefore, there is provided a pharmaceutical formulation comprising a compound of formula (II) or (III) alone, or in combination with a 2,4-diamino-5-benzylpyrimidine and/or a sulphonamide, in admixture with a pharmaceutically acceptable carrier. In yet another aspect the present invention provides a method of making a pharmaceutical formulation by admixing the compound of formula (II) or (III) alone, or in combination with a 2,4-diamino-5-benzylpyrimidine and/or a sulphonamide with a carrier by known techniques.

Any of the aforementioned antimicrobial compounds may be presented in the form of their pharmaceutically acceptable salts. Examples of pharmaceutically acceptable salts are those derived from mineral or organic acids, for example hydrochloric acid, hydrobromic acid, sulphuric acid, acetic acid, citric acid, tartaric acid, lactic acid, maleic acid, or salicyclic acid, or especially for the sulphonamide, of a base, such as sodium or potassium hydroxide. Salts which are not pharmaceutically acceptable may be rendered so by a conventional metathetical reaction.

In yet another aspect, the present invention provides a method of treating humans and other animals suffering from microbial infections which comprises administering a non-toxic effective antimicrobial treatment amount of a compound of formula (II) or (III), or preferably administering a pharmaceutical formulation comprising said amount of a compound of formula (II) or (III) and a pharmaceutically acceptable carrier, to the infected human or other animal.

In yet a further aspect, the present invention provides a method of treating humans and other animals suffering from microbial infections which comprises administering a composition comprising an effective potentiating amount of a compound of formula (II) or (III), in combination with an effective amount of a 2,4-diamino-5-benzylpyrimidine or a sulphonamide, or both, or preferably administering a pharmaceutical formulation comprising the said composition and a pharmaceutically acceptable carrier, to the infected human or other animal.

A suitable dose range for a compound of formula (II) of formula (III) (either alone or with a sulphonamide and/or pyrimidine derivative) for the treatment of microbial infections lies in the range of 1 mg to 100 mg/kg body weight.

For compounds of formula (III) when used incorporated in animal feeds for the treatment or prophylaxis of protozoal infections a suitable dose range is from 100 to 400 ppm of active ingredient.

Further advantages of the present invention can be ascertained from the following Examples which should not be construed as limiting the scope of the invention in any way.

EXAMPLE 1

8-Amino-3,5-diphenyl-1-methyl-1H-pyrimido{4,5-c}-1,2-diazepin-6(7H)-one (I) ($R^1 = C_6H_5$; $R^2 = C_6H_5$)

To a stirred, refluxing mixture of 6-(1-methylhydrazino)isocytosine hemihydrate (1.00 g) in methanol (100 ml) was added 1,3-diphenyl-1,3-propanedione (2.05 g). After 236 hours the orange solution was allowed to cool to room temperature.

The solution was concentrated under vacuum onto silica gel (5.0 g) that was added to a column of silica gel (90 g) in hexane. Elution of the column with benzene, a 3:1 benzene:chloroform mixture, chloroform, and ethyl acetate effected separation of the desired product that came off in the 3:1 benzene:chloroform mixture, chloroform, and ethyl acetate, yield 1.01 g. Yellow solid was obtained after recrystallisation from carbon tetrachloride, yield 0.64 g (29%): mp 205°–220° dec.; nmr (DMSO-d$_6$) $\delta$3.12(s, 3H), 6.69(s, 1H), 6.77(br. s, 2H), 7.2–7.6(m, 8H), 7.6–8.0(m, 2H), 10.6(br. s, 1H); uv $\lambda$max (CH$_3$OH) 255.5 nm ($\epsilon$22,200), 285(26,400), 385(700), Mass spectrum (210° C.): M, m/e 343. The following accurate mass was determined: 343.1437 (C$_{20}$H$_{17}$N$_5$O).

Anal. Calcd. for C$_{20}$H$_{17}$N$_5$O.0.022 CCl$_4$; C,69.35%; H,4.94%; N,20.20%; Cl, 0.90%. Found: C,69.43%; H,5.09%; N,20.15%; Cl,0.90%.

EXAMPLE 2

8-Amino-1,3,5-trimethyl-1H-pyrimido{4,5-c}-1,2-diazepin-6(7H)-one (I) ($R^1 = CH_3$; $R^2 = CH_3$)

To a stirred, refluxing mixture of 6-(1-methylhydrazino)isocytosine hemihydrate (1.00 g) in methanol (100 ml) was added acetylacetone (0.913 g). After 48 hours the resulting orange solution was allowed to cool to room temperature and stand overnight.

The solution was concentrated by boiling to 25 ml and was then allowed to cool to room temperature. After 2 hours the slightly cloudy solution was filtered, and the clear filtrate was concentrated by boiling to 15 ml after which time it was allowed to cool to room temperature and stand overnight. No crystallisation occurred until after 24 hours when the solution was suddenly jarred. After an additional 2 hours yellow crystals were collected, washed quickly with methanol (5 ml) and hexane (10 ml), and dried under vacuum at 75° C. to yield the desired product 0.541 g (41%): mp 250°–253° dec; nmr (DMSO-d$_6$) $\delta$1.84(s, 3H), 2.06 (d, 3H, J = 1 Hz), 2.88(s, 3H), 5.89 (q, 1H, J = 1 Hz), 6.67(br. s, 2H), 10.58(br. s, 1H). On a different batch of product a Nuclear Overhauser Effect of 25% was observed for the aromatic

quartet at 5.89 $\delta$ upon irradiation of the aromatic —CH$_3$ doublet at 2.06 $\delta$. A Nuclear Overhauser Effect of 19% was observed for the aromatic

quartet at 5.89 $\delta$ upon irradiation of the ring —CH$_3$ singlet at 1.84 $\delta$. A coupling experiment showed that absorption at 2.065 and 5.895 were coupled to each other; uv $\lambda$ max (CH$_3$OH) 233.5 nm sh ($\epsilon$ 11,400), 267(17,900), 302(9,900), 348(1,300); pKa 9.11 and 3.27. Mass spectrum of a different batch: M, m/e 219, 43%; m/e 178, 100%.

Anal. Calcd. for C$_{10}$H$_{13}$N$_5$O: C,54.78%; H,5.98%; N,31.95%. Found: C,54.96; H,5.99%; N, 31.72%.

EXAMPLE 3

8-Amino-3-carbomethoxy-5-(3-hydroxyphenyl)-1-methyl-1H-pyrimido{4,5-c}-1,2-diazepin-6(7H)-one (I) ($R^1 = C_6H_4OH$; $R^2 = CO_2CH_3$)

To a stirred, refluxing mixture of 6-(1-methylhydrazino)isocytosine hemihydrate (1.76 g) in methanol (176 ml) was added methyl m-hydroxybenzoylpyruvate (2.88 g). After 22 hours precipitated solid was collected from the hot mixture, yield 0.282 g.

The filtrate was brought to boiling and was concentrated to 75 ml when precipitated solid was noticed to be present. The mixture was allowed to cool to room temperature and stand for several hours. Brownish-orange solid was collected, washed with two portions of methanol (10 ml each), and dried under vacuum at 80° C. to yield the desired product 1.80 g (49%): mp >275° dec; nmr (DMSO-d$_6$) $\delta$ 3.11(s, 3H), 3.79(s, 3H), 6.50(s, 1H), 6.6–7.4 (m, 6H), 9.22(br. s, 1H), 10.77(br. s, 1H); uv $\lambda$ max (CH$_3$OH) 244.5 nm ($\epsilon$19,600), 280.5 sh (16,700), 305(20,500), 424(700).

Anal. Calcd. for C$_{16}$H$_{15}$N$_5$O$_4$: C, 56.30%; H, 4.43%; N, 20.52%. Found: C, 56.34%; H, 4.48%; N, 20.56%.

EXAMPLE 4

8-Amino-3-carbomethoxy-1-methyl-5-(3-pyridyl)-1H-pyrimido{4,5-c}-1,2-diazepin-6(7H)-one (I) ($R^1 = $ 3-pyridyl; $R^2 = CO_2CH_3$)

To a stirred, refluxing mixture of 6-(1-methylhydrazino)isocytosine hemihydrate (1.00 g) in methanol (100 ml) was added methyl 2,4-dioxo-4-(3-pyridyl)butyrate (1.51 g). After 17½ hours brown solid was collected from the hot mixture, washed with two portions of methanol (10 ml each), and dried under vacuum at 75° C. to yield the desired product 1.11 g (56%): mp 258°–272° dec; nmr (DMSO-d$_6$) $\delta$ 3.11(s, 3H), 3.79(s, 3H), 6.56(s, 1H), 6.98(br. s, 2H), 7.1–7.8(m, 2H), 8.3–8.6(m, 2H), 10.9(br. s, 1H); nmr (CF$_3$COOH) δ 3.53(s, 3H), 4.12(s, 3H), 7.13(s, 1H), 8.0–8.3(m, 1H), 8.5–9.0(m, 3H); uv λ max (CH$_3$OH) 244.5 nm (ε 21,800), 284 sh(16,500), 307.5(17,500), 454(900).

Anal. Calcd. for C$_{15}$H$_{14}$N$_6$O$_3$: C, 55.21%; H, 4.32%; N, 25.76%. Found: C, 55.19%; H, 4.29%; N, 25.84%.

EXAMPLE 5

8-Amino-3-carbethoxy-1-methyl-5-phenyl-1H-pyrimido-{4,5-c}-1,2-diazepin-6(7H)-one (I) (R$^1$=C$_6$H$_5$; R$^2$=CO$_2$C$_2$H$_5$)

To a stirred mixture of 6-(1-methylhydrazino)isocytosine hemihydrate (1.00 gl) in absolute ethanol at 65°–70° was added ethyl benzoylpyruvate (2.01 g). After 101 hours some precipitated solid was collected from the hot mixture. After a further ½ hour an additional small amount of solid was filtered from from cooled filtrate.

After the filtrate had stood overnight, precipitated pale orange solid was collected, washed with 5 ml of chloroform and 10 ml of hexane, and dried under vacuum at 75° to yield the desired product 0.796 g. Yellow solid was obtained after two recrystallisations from benzene, yield 0.200 g (9%): mp 240.5°–242.5° dec;

Nmr (DMSO-d$_6$) δ 1.28(t, 3H), 3.12(s, 3H), 4.26(q, 2H), 6.52(s, 1H), 6.89(br.s, 2H), 7.28(br. s, 5H), 10.7 (br. s, 1H); uv λ max (CH$_3$OH) 243.5 nm (ε 19,400), 294(20,200), 419.5(600). Mass spectrum (180° C.): M, m/e 339, 35%; m/e 240, 100% (M—C$_2$H$_5$O$_2$CCN). The following accurate mass was determined: 240.1008 (C$_{13}$H$_{12}$N$_4$O). The most prominent metastable ion for the molecular ion was m/e 339→m/e 240.

Anal. Calcd. for C$_{17}$H$_{17}$N$_5$O$_3$.0.20C$_6$H$_6$: C, 61.58%; H, 5.17%; N, 19.73%. Found: C, 61.72%; H, 5.29%; N, 19.88%.

EXAMPLE 6

8-Amino-3-carbomethoxy-1-methyl-5-(3,4,5-trimethoxyphenyl)-1H-pyrimido{4,5-c}-1,2-diazepin-6(7H)-one (I) (R$^1$=C$_6$H$_2$(OCH$_3$)$_3$; R$^2$=CO$_2$CH$_3$)

To a stirred, refluxing mixture of 6-(1-methyl hydrazino)isocytosine hemihydrate (1.00 g) in methanol (100 ml) was added methyl 3,4,5-trimethoxybenzoylpyruvate (2.70 g). After 40 hours precipitated solid was collected from the hot mixture to yield 0.360 g of product.

The filtrate was concentrated under vacuum to 2.8 g of solid that was stripped onto silica gel (5.0 g) that was added to a column of silica gel (90 g) in hexane. Elution of the column with benzene, benzene:chloroform mixtures, chloroform, a 1:1 chloroform:ethyl acetate mixture, ethyl acetate, and finally a 9:1 ethyl acetate:methanol mixture effected separation of the desired product that came off in the 9:1 ethyl acetate:methanol mixture, yield 1.57 g. Tiny, orange crystals were obtained after recrystallisation from methanol to yield 1.15 g (45%) of product; mp 258°–260° dec.; nmr (DMSO-d$_6$) δ 3.09(s, 3H), 3.67, 3.74, and 3.77 (overlapping s's, 12H), 6.47(s, 2H), 6.51(s, 1H), 6.87(br. s, 2H), 10.8 (br. s, 1H); uv λ max (CH$_3$OH) 239 nm sh (ε 19,900), 307.5 (24,600), 421(800). Mass spectrum of a different batch (210° C.): M, m/e 415, 56%; m/e 330, 57%; m/e 315, 100%.

Anal. Calcd. for C$_{19}$H$_{21}$N$_5$O$_6$: C, 54.93%; H, 5.10%; N, 16.86%; Found: C, 54.99%; H, 5.15%; N, 16.82%.

The following compounds were prepared in a manner similar to that of Example 6:

EXAMPLE 7

8-Amino-3-carbethoxy-1-methyl-5-(2,4-dimethoxyphenyl)-1H-pyrimido{4,5-c}-1,2-diazepin-6(7H)-one (I) (R$^1$=C$_6$H$_3$(OCH$_3$)$_2$; R$^2$=CO$_2$C$_2$H$_5$)

Refluxing absolute ethanol was used as solvent. Precipitated solid was collected after 42 hours. Product was eluted from a column with 9:1 ethyl acetate:methanol.

Yield after recrystallisation from benzene (28%): mp 187°–196° dec.; nmr (DMSO-d$_6$) δ 1.27(t, 3H), 3.09(s, 3H), 3.64(s, 3H), 3.77(s, 3H), 4.24(q, 2H), 6.4–7.1(m, 6H), 10.5(br s, 1H); uv λ max (CH$_3$OH) 246.5 nm (ε 20,500), 311.5(21,700), 345.5 sh (5,100) 420 sh (900).

Anal. Calcd. for C$_{19}$H$_{21}$N$_5$O$_5$.0.43 C$_6$H$_6$: C, 59.86%; H, 5.49%; N, 16.18%. Found: C, 59.89%; H, 5.54%; N, 16.33%.

EXAMPLE 8

8-Amino-3-carbethoxy-1-methyl-5-(3,4-dimethoxyphenyl)-1H-pyrimido{4,5-c}-1,2-diazepin-6(7H)-one (I) (R$^1$=C$_6$H$_3$(OCH$_3$)$_2$; R$^2$=CO$_2$C$_2$H$_5$)

Absolute ethanol (65°–70° C.) was used as solvent. Precipitated solid was collected after 112 hours. Product was eluted from a column with ethyl acetate. Yield after dissolution in ethyl acetate and precipitation with hexane (7%): mp 162° dec; nmr (DMSO-d$_6$) δ 1.27(t, 34), 3.10(s, 3H), 3.72(s, 3H), 3.75 (s, 3H), 4.24(q, 2H), 6.50(s, 1H), 6.6–7.2(m, 5H), 10.8(br s, 1H); uv λ max (CH$_3$OH) 245 nm (ε 20,800), 309 (21,900).

Anal. Calcd. for C$_{19}$H$_{21}$N$_5$O$_5$.0.1 CH$_3$CO$_2$C$_2$H$_5$.0.4 H$_2$O: C, 56.09%; H, 5.48%; N, 16.86%. Found: C, 56.16%; H, 5.23%; N, 16.86%.

EXAMPLE 9

8-Amino-3-carbethoxy-1,5-dimethyl-1H-pyrimido{4,5-c}-1,2-diazepin-6(7H)-one (I) (R$^1$=CH$_3$; R$^2$=CO$_2$C$_2$H$_5$)

To a stirred, refluxing mixture of 6-(1-methylhydrazino)isocytosine hemihydrate (5.00 g) in methanol (500 ml) was added ethyl acetylpyruvate (5.78 g). After 65 hours the solution was concentrated by boiling to 40 ml and was allowed to stand overnight.

The solution was concentrated under vacuum to 9.7 g of pasty solid that was stripped onto silica gel (10 g) that was then added to a column of silica gel (400 g) in hexane. Elution of the column with a 1:1 benzene:chloroform mixture, chloroform, chloroform:ethyl acetate mixtures, ethyl acetate, and a 4:1 ethyl acetate:methanol mixture effected separation of desired product that came off in ethyl acetate, yield 3.95 g. Orange crystals were obtained after recrystallisation from ethyl acetate, yield 2.52 g (30%): mp 244°–245° dec; nmr (DMSO-d$_6$) δ 1.24 (t, 3H, J=7.5 Hz), 2.12 (d, 3H, J=1 Hz), 3.03(s, 3H), 4.22(q, 2H, J=7.5 Hz), 6.18(q, 1H, J=1 Hz), 6.83(br s, 2H), 10.8(br, s, 1H). On a different batch of product, a Nuclear Overhauser Effect of 32% was observed for the aromatic

quartet at 6.18 δ upon irradiation of the aromatic —CH$_3$ doublet at 2.12 δ; uv of a different batch λ max (CH$_3$OH) 245 nm (ε 17,200), 284 sh (11,300), 306(14,100), 410(600). Mass spectrum of a different batch (155° C.): M, m/e 277, 29%; m/e 178, 100% (M-NCCO$_2$C$_2$H$_5$). The following accurate masses were determined 277.1163(C$_{12}$H$_{15}$N$_5$O$_3$), 178.0843 (C$_8$H$_{10}$N$_4$O).

Anal. Calcd. for C$_{12}$H$_{15}$N$_5$O$_3$: C, 51.98%; H, 5.45%; N, 25.26%. Found: C, 51.91%; H, 5.45%; N, 25.18%.

EXAMPLE 10

8-Amino-5-carbethoxy-1,3-dimethyl-1H-pyrimido{4,5-c}-1,2-diazepin-6(7H)-one (I) (R$^1$=CO$_2$C$_2$H$_5$; R$^2$=CH$_3$)

The isomer of the compound just described was prepared and isolated in the same experiment.

This product came off the column in ethyl acetate and a 4:1 ethyl acetate:methanol mixture after its isomer (previous Example) had came off, yield 3.13 g. Pale yellowish-orange crystals were obtained after two recrystallisations from carbon tetrachloride, yield 0.942 g (11%): mp 196° dec; nmr (DMSO-d$_6$) δ 1.16(t, 3H), 1.93(s, 3H), 2.91(s, 3H), 4.06(q, 2H), 6.39(s, 1H), 6.83(br s, 2H), 10.8(br s, 1H), uv of a different batch λ max (CH$_3$OH) 241.5 nm (ε 14,500), 295(14,200), 305.5 sh (13,100), 387(900). Mass spectrum of a different batch (160°): M, m/e 277, 70%; m/e 236, 100% (M—CH$_3$CN). The following accurate masses were determined: 277.1170 (C$_{12}$H$_{15}$N$_5$O$_3$), 236.0902 (C$_{10}$H$_{12}$N$_4$O$_3$).

Anal. Calcd. for C$_{12}$H$_{15}$N$_5$O$_3$.0.45 CCl$_4$: C, 43.15%; H, 4.36%; N, 20.21%; Cl, 18.42%. Found: 42.87%; H, 4.38%; N, 20.43%; Cl, 18.07%.

EXAMPLE 11

2,7-Diamino-S-methyl-5-phenylpyrido{2,3-d}pyrimidin-4(8H)-one (XVII) (R$^8$=C$_6$H$_5$)

To 8-amino-3-carbethoxy-1-methyl-5-phenyl-1H-pyrimido{4,5-c}-1,2-diazepin-6(7H)-one (2.9 g) was added N NaOH (100 ml), and a solution resulted after the mixture was swirled. After 45 minutes the solution was acidified with conc. HCl until pH 2.5–3.0 was reached. Precipitated yellow solid was collected, washed with water (3×15 ml), and dried under vacuum at 70° C., yield 2.4 g of product. This solid was shown by nmr to be the corresponding carboxylic acid of the starting ester.

A 2.3 g sample of solid was suspended in boiling methyl cellosolve (175 ml), and the resulting dark brownish-red solution quickly became orangish-yellow in colour. The solution was concentrated to 130 ml when solid precipitated. The mixture was allowed to cool to room temperature and stand for 2 hours. Off-white solid was collected, washed with methyl cellosolve (2×15 ml) and methanol (4×15 ml), and dried under vacuum at 70° C., yield 1.28 g (49%) of product: mp >300°; nmr (CF$_3$COOH) δ 4.08(s, 3H), 6.68(s, 1H), 7.0–7.8(m, 7H); nmr (DMSO-d$_6$) δ 3.64(s, 3H), 5.93(s, 1H), 6.76(br s, 2H), 7.1–7.4(m, 5H), 7.8* (very br s, 2H); uv λ max (CH$_3$OH) 216 nm (ε 35,300), 258 sh (9,400), 290.5(13,000), 348(17,400). Mass spectrum (250°): M, m/e 267, 100%; m/e 266, 26%; m/e 140, 10%. The following accurate mass was determined: 267.1120(C$_{14}$H$_{13}$N$_5$O).

*This chemical shift was estimated by guessing the midpoint of a very broad integral.

Anal. Calcd. for C$_{14}$H$_{13}$N$_5$O.0.08 CH$_3$OCH$_2$CH$_2$OH. 0.2 H$_2$O: C, 61.75%; H, 5.11%; N, 25.29%. Found: C, 61.76%; H, 5.30%; N, 25.32%.

EXAMPLE 12

2,7-Diamino-8-methyl-5-(3-hydroxyphenyl)pyrido{2,3-d}-pyrimidin-4(8H)-one (XVII) (R$^8$=C$_6$H$_4$OH)

To 8-amino-3-carbomethoxy-1-methyl-5-(3-hydroxyphenyl)-1H-pyrimido{4,5-c}-1,2-diazepin-6(7H)-one (4.79 g) was added N NaOH (190 ml), and a solution resulted after the mixture was swirled. After 1 hour 15 minutes the solution was acidified with conc. HCl until pH 1 was reached. Precipitated solid was collected, washed with water (3×10 ml), and dried under vacuum at 80° C. to yield 4.49 g of product. This solid was shown by nmr to be the corresponding carboxylic acid of the starting ester.

The carboxylic acid was boiled for 2½ hours in methyl cellosolve (50 ml), and product was collected from a hot mixture, washed with methyl cellosolve (15 ml) and methanol (3×10 ml), and dried under vacuum at 80°, yield (60%): mp >300°; nmr (CF$_3$COOH): δ 4.07(s, 3H), 6.69(s, 1H), 7.0–7.6(m, 6H); uv λ max (CH$_3$OH) 217.5 nm (ε 42,300), 247 sh (10,700), 292 (14,300), 338 weak sh (16,200), 347(18,400).

Anal. Calcd. for C$_{14}$H$_{13}$N$_5$O$_2$: C, 59.35%; H, 4.63%; N, 24.72%. Found: C, 59.24%; H, 4.65%; N, 24.70%.

EXAMPLE 13

2,7-Diamino-8-methyl-5-(3,4,5-trimethoxyphenyl)-pyrido{2,3-d}pyrimidin-4(8H)-one (XVII) (R$^8$=C$_6$H$_2$(OCH$_3$)$_3$)

Following the general procedure of Example 11, the above compound was synthesised.

Yield (55%); mp>300°; nmr (CF$_3$COOH) δ 4.00 (s, 6H), 4.09(s, 6H), 6.73(s, 1H), 6.76(s, 2H), 7.26 (br s, 2H); uv λ max (CH$_3$OH) 261.5 nm (ε 10,400), 293(14,000), 339 weak sh (16,900), 348(18,800). Mass spectrum (260°): M, m/e 357, 100%; m/e 342, 16% (M—CH$_3$); m/e 327, 4% (M—CH$_2$O and M—C$_2$H$_6$); m/e 317, 1% (M—C$_2$H$_2$N); m/e 316, 1% (M—C$_2$H$_3$N).

The following accurate masses were determined: 357.1432(C$_{17}$H$_{19}$N$_5$O$_4$), 342.1203(C$_{16}$H$_{16}$N$_5$O$_4$), 327.1333 (C$_{16}$H$_{17}$N$_5$O$_3$), 327.0969(C$_{15}$H$_{13}$N$_5$O$_4$), 317.1265(C$_{15}$H$_{17}$N$_4$O$_4$), 316.1164(C$_{15}$H$_{16}$N$_4$O$_4$).

Anal. Calcd. for C$_{17}$H$_{19}$N$_5$O$_4$: C, 57.13%; H, 5.36%; N, 19.60%. Found: C, 57.15%; H, 5.41%; N, 19.52%.

The reaction was shown to procede through the intermediate carboxylic acid. This acid was identified by nmr and gave the following microanalysis: Calcd. for C$_{18}$H$_{19}$N$_5$O$_6$: C, 53.86; H, 4.77; N, 17.45%. Found: C, 53.90; H, 4.80; N, 17.34%.

EXAMPLE 14

2,7-diamino-5,8-dimethylpyrido{2,3-d}pyrimidin-4(8H)-one

(XVII) ($R^8 = CH_3$)

Following the general procedure of Examples 11 and 12, the above compound was synthesized.

Yield (68%): mp >300°; nmr ($CF_3COOH$) δ 2.81 (s, 3H), 4.00(s, 3H), 6.65(s, 1H), 6.96(br, s, 2H); nmr (DMSO-$d_6$) δ 2.54 (s, 3H), 3.61(s, 3H), 5.98(s, 1H), 6.49 (br s, 2H), 7.5* (very br s, 2H); uv λ max ($CH_3OH$) 218 nm (ε 31,100), 253 (4,300), 290.5 (8,400), 327.5 sh (17,300), 337(20,400). Mass spectrum (250° C.): M, m/e 205, 100%; m/e 165, 4% (M—$C_2H_2N$); m/e 164, 3% (M—$C_2H_3N$). The following accurate masses were determined: 205.0962($C_9H_{11}N_5O$), 165.0785($C_7H_9N_4O$), 164.0709($C_7H_8N_4O$).

*This chemical shift was estimated by guessing the midpoint of a very broad integral.

Anal. Calcd. for $C_9H_{11}N_5O$: C, 52.67; H, 5.40; N, 34.13%. Found: C, 52.50; H, 5.40; N, 34.05%.

EXAMPLE 15

2,7-Diamino-8-methyl-5-(3-pyridyl)pyrido{2,3-d}-pyrimidin-4(8H)-one

(XVII) ($R^8 = 3$-pyridyl)

The above compound was synthesised following the general procedure of Examples 11 and 12.

Yield (27%): mp 301°–304° dec; nmr ($CF_3COOH$) δ 4.12(s, 3H), 6.85(s, 1H), 7.69(br s, 2H), 8.1–8.4 (m, 1H), 8.6–9.1 (m, 3H); uv λ max ($CH_3OH$) 215 nm (ε 34,800), 264.5(11,300), 290(10,800), 352.5 (15,900). Mass spectrum: M, m/e 268, 100%; m/e 240, 10%; m/e 228, 3% (M-$C_2H_2N$); m/e 227, 3% (M-$C_2H_3N$ and M-$CHN_2$). The following accurate masses were determined: 268.1072 ($C_{13}H_{12}N_6O$), 228.0885 ($C_{11}H_{10}N_5O$), 227.0923 ($C_{12}H_{11}N_4O$), 227.0811 ($C_{11}H_9N_5O$).

Anal. Calcd. for $C_{13}H_{12}N_6O \cdot 0.24\ CH_3OCH_2CH_2OH \cdot 0.18\ H_2O$: C, 56.86%; H, 4.97%; N, 29.00%. Found: C, 56.82%; H, 5.08%; N, 29.05%.

EXAMPLE 16

6-Amino-1,3-dimethyl-1H-pyrazolo{3,4-d}pyrimidin4(5H)-one

(XIX) ($R^9 = CH_3$)

A mixture of 8-amino-1,3,5-trimethyl-1H-pyrimido{4,5-c}-1,2-diazepin-6(7H)-one (219 mg) and N hydrochloric acid (3 ml) was heated using a hot water bath (>85° C.) for 2 hours. During that period a solution formed before crystals gradually began to separate. The mixture stood at room temperature overnight before the straw-coloured crystals were collected, washed with water and dried under vacuum (70° C.) to yield 140 mg (78%) of analytically pure product: mp >300°; nmr (DMSO-$d_6$) δ 2.28(s, 3H), 3.60(s, 3H), 6.52(br s, 2H), 10.30(br s, 1H); uv λ max ($CH_3OH$) 217 nm (ε 26,800), 254(13,000). Mass spectrum (120° C., 70 ev): M, m/e 179, 100%.

Anal. Calcd. for $C_7H_9N_5O$: C, 46.92%; H, 5.06%; N, 39.09%. Found: C, 46.68%; H, 5.11%; N, 38.94%.

The following compounds (Examples 17, 18 and 19) were prepared by similar acid-catalysed hydrolysis conditions:

EXAMPLE 17

6-Amino-1-methyl-3-phenyl-1H-pyrazolo{3,4-d}pyrimidin4(5H)-one

(XIX) ($R^9 = C_6H_5$)

Method A

Starting material, 8-amino-3-carbethoxy-1-methyl-5-phenyl-1H-pyrimido{4,5-c}-1,2-diazepin-6(7H)-one; reaction time, 3 hours; yield after recrystallisation from ethanol, 43%: mp>300°; nmr (DMSO-$d_6$) δ 3.73 (s, 3H), 6.65 (br s, 2H), 7.30–7.50(m, 3H), 8.25–8.42 (m, 2H), 10.90(br s, 1H); uv λ max($CH_3OH$) 246 nm (ε 29,900), 280 sh (8,400). Mass spectrum (170°, 70 ev): M, m/e 241, 100%.

Anal. Calcd. for $C_{12}H_{11}N_5O$: C,59.74%; H,4.60%; N,29.03%. Found: C,59.60%; H,4.66%; N,28.92%.

Method B

Starting material, 8-amino-3,5-diphenyl-1-methyl-1H-pyrimido {4,5-c}-1,2-diazepin-6(7H)-one; reaction time, 3 hours; yield after washing with ether,* 29%: spectral data same as that recorded above.

* A competing reaction produced 1,3-diphenyl-1,3-propanedione which was isolated from the ether wash in 50% yield.

Anal. Found: C,59.47%; H,4.59%; N,28.77%.

EXAMPLE 18

6-Amino-1-methyl-3-(3,4,5-trimethoxyphenyl)-1H-pyrazolo{3,4-d}pyrimidin-4(5H)-one

(XIX) ($R^9 = C_6H_2(OCH_3)_3$)

Starting material, 8-amino-3-carbomethoxy-1-methyl-5-(3,4,5-trimethoxyphenyl)-1H-pyrimido{4,5-c}-1,2-diazepin-6(7H)-one; reaction time, 3 hours; yield after subsequent neutralization of the collected, crude product with 0.1 N sodium hydroxide and recrystallisation from methanol, 40%: mp 183°–184°; nmr (DMSO-$d_6$) δ 3.70(s, 3H), 3.77(s, 3H), 3.85(s, 6H), 6.70(br s, 2H), 7.87(s, 2H), 10.43(br s, 1H) plus methanol δ 3.19(d, 3H, J=5 Hz), 4.04(q, 1H, J=5 Hz); uv λ max ($CH_3OH$) 222.5 nm (ε 33,200), 254.5 (24,100), 282 (14,800). Mass spectrum (160°, 70 ev): M, m/e 331, 100%*.

* This mass spectrum was obtained for a different batch prepared by the same method.

Anal. Calcd. for $C_{15}H_{17}N_5O_4 \cdot CH_3OH$: C,52.89%; H,5.83%; N,19.27%. Found: C,52.73%; H,5.63%; N,19.45%.

EXAMPLE 19

6-Amino-3-(3-hydroxyphenyl)-1-methyl-1H-pyrazolo{3,4-d}pyrimidin-4(5H)-one.0.55 methanolate.0.16 hydrate

(XIX) ($R^9 = C_6H_4OH$)

Starting material, 8-amino-3-carbomethoxy-5-(3-hydroxyphenyl)-1-methyl-1H-pyrimido {4,5-c}-1,2-diazepin-6(7H)-one; reaction time, 2 hours. A solid impurity was removed by filtration before the crude product was subsequently precipitated from the mother liquor by neutralization with 4 N sodium hydroxide solution, collected by filtration, washed with water, dried under vacuum (70°) and recrystallised twice from methanol; yield,* 21%: mp>300°; nmr (DMSO-$d_6$); δ 3.74(s, 3H), 6.67 m and 6.80 m (3H), 7.21(t, 3H, J=8 Hz), 7.81 m and 7.89 m (2H), 9.36(s, 1H), 10.56(br s, 1H), plus methanol (0.5 mol) 3.19(d, 3H, J=5 Hz), 4.04(q, 1H, J=5 Hz) and water δ 3.30; uv λ max (CH$_3$OH) 248 nm ($\epsilon$ 26,400), 284 sh (8,800). Mass spectrum (150°, 70 ev): M, m/e 257, 100%.

* Other batches obtained during recrystallisation provided evidence for an overall yield of ca. 40%.

Anal. Calcd. for C$_{12}$H$_{11}$N$_5$O$_2$.0.55 CH$_3$OH.0.16H$_2$O: C,54.27%; H,4.91%; N,25.22%. Found: C,54.25%; H,4.82%; N,25.20%.

EXAMPLE 20

4-Acetonyl-7-amino-1-methylpyrimidó{4,5-c}pyridazine-3,5-(1H, 2H)-dione (XXI) IR$^{12}$=CH$_3$)

A solution of 8-amino-5-carbomethoxy-1,3-dimethyl-1H-pyrimido{4,5-c}-1,2-diazepin-6(7H)-one (0.407 g) in a strongly acidic (pH$\leq$2), aqueous solution of HCl (13 ml) was allowed to stand for one day. Precipitated brownish-orange solid was collected, washed with water, and dried under vacuum at 75° C. to yield 0.080 g of a product mixture.

After an additional three days brownish-orange solid in the filtrate was collected, washed with two portions of water (2×2.5 ml) and dried under vacuum at 75° C. to yield 0.097 g (25%) of product; nmr (CF$_3$COOH) $\delta$ 2.60(s, 3H), 4.28(s, 3H), 4.85(s, 2H), 6.92(br's, 2H). Qualitative uv data and the nmr data suggested that the compound had the structure named above.

EXAMPLE 21

7-Amino-1,4-dimethylpyrimido{4,5-c}pyridazine-3,5-(1H, 6H)-dione (XXIII)

4-Acetonyl-7-amino-1-methylpyrimido{4,5-c}-pyridazine-3,5-(1H, 2H)-dione (0.054 g) was dissolved in boiling methyl cellosolve (1 l), and the solution was concentrated to 40 ml when precipitated solid was noticed to be present. The mixture was allowed to cool to room temperature and stand overnight. Yellowish-green solid was collected, washed with methyl cellosolve (10 ml) methanol (2 ml), and dried under vacuum at 75° C. to yield 0.018 g (35%) of product: nmr (CF$_3$COOH) $\delta$ 3.03(s, 3H), 4.26(s, 3H), 6.83(br s, 2H).

EXAMPLE 22

The antibacterial activity against *Staphylococcus aureus* of trimethoprim (TMP) and sulphamethoxazole (SMX) alone and in combination with compounds of formula (II) were compared.

The results shown in the table are expressed as an activity index which is:

$$\frac{ED_{50} \text{ of } SMX \text{ (or } TMP\text{) alone}}{ED_{50} \text{ of } SMX \text{ (or } TMP\text{) plus compound of formula (II)}}$$

the effect of the compounds being measured by viable counts after 24 hours incubation of 10$^6$ organisms per ml.

In this test, the compounds of formula (II) were present at 50 $\mu$g/ml.

An activity index $\leq$2 is indicative of substantial potentiation:

| Compound of formula II | | | |
|---|---|---|---|
| R$^3$ | R$^4$ | TMP | SMX |
| C$_6$H$_5$ | CO$_2$C$_2$H$_5$ | 2.0 | >2.8 |
| C$_6$H$_4$OH(3) | CO$_2$CH$_3$ | 0.9 | 2.7 |

EXAMPLE 23

The anti-coccidial activity of compounds of formula (III) alone and in combination with a mixture of diaveridine (DV) and sulphaquinoxaline (SQX) in vitro was tested according to the following procedure.

Using standard test procedures employing primary explant cultures of chick embryo liver cells and a suspension of *Eimeria Tenella* (Weybridge) sporozites the activity of the compounds was determined at various concentrations. In the above test, each test compound was used either alone or in combination with sulphaquinoxaline (0.01 $\mu$g/ml) and diaveridine (0.031 $\mu$g/ml). It should be noted that the minimum active anti-coccidial amounts of sulphaquinoxaline and diaveridine are 0.024 $\mu$g/ml and 0.098 $\mu$g/ml respectively.

The following results were obtained wherein activity is expressed as follows:

5 = No parasite development
4 = 1–25% parasite development
3 = 26–50% parasite development
2 = 51–75% parasite development
1 = 76–95% parasite development
0 = 95–100% parasite development

| Compound of formula (III) | | Activity (concentration $\mu$g/ml) | |
|---|---|---|---|
| R$^3$ | R$^4$ | Alone | With DV/SOX |
| OMe (3,5-dimethoxyphenyl with OMe) | CO$_2$C$_2$H$_5$ | 4(100) 4(25) 2(6.25) 0(1.56) | 5(100) 5(25) 3(6.25) 2(1.56) |
| OMe, MeO, OMe (3,4,5-trimethoxyphenyl) | CO$_2$CH$_3$ | 3(100) 3(25) 3(6.25) 2(1.56) | 5(100) 4(25) 3(6.25) 3(1.56) |
| C$_6$H$_5$ | C$_6$H$_5$ | 4(25) | 4(25) |

EXAMPLE 24

Compounds of formula (III) were tested for anti-coccidial activity in vivo in combination with diaveridine (DV) and sulphaquinoxaline (SQX), each at 20 ppm, according to the following procedure.

Groups of five, one week old chicks were each injected orally with 6,000 sporulated o cysts of the Weybridge strain of *Eimeria tenella*. Drugs were administered in LD 5 chick mash deficient in Vitamin K, beginning on the day of infection and continuing for 7 days. On the sixth day after infection, caecal lesions of surviving chicks were scored on a scale of 0, 1, 2 or 3 and any dead chicks were scored as 4. The following results were obtained:

| Compound of formula (III) | | Concn. in diet (ppm) | Concn. DV in diet (ppm) | Concn. SQX in diet (ppm) | Lesion score |
|---|---|---|---|---|---|
| R$^3$ | R$^4$ | | | | |
| — | — | — | 20 | 20 | 2.2 |

-continued

| Compound of formula (III) | | Concn. in diet (ppm) | Concn. DV in diet (ppm) | Concn. SQX in diet (ppm) | Lesion score |
|---|---|---|---|---|---|
| $R^3$ | $R^4$ | | | | |
| OMe, OMe (dimethoxy phenyl) | $CO_2C_2H_5$ | 200 | 20 | 20 | 1.2 |
| MeO, OMe, OMe (trimethoxy phenyl) | $CO_2CH_3$ | 200 | 20 | 20 | 0.6 |

EXAMPLE 25

By standard techniques the $LD_{50}$ values of the following compounds of formula (I) were determined in mice.

| Compound of formula (I) | | |
|---|---|---|
| $R^1$ | $R^2$ | $LD_{50}$ i.p. in mice |
| MeO, OMe, OMe (trimethoxy phenyl) | $CO_2CH_3$ | > 500 mg/kg |
| $CH_3$ | $CH_3$ | ≈ 500 mg/kg |

EXAMPLE 26

(i) Tablets containing the following amounts of active ingredients are prepared by standard methods of pharmacy.
(A) Compound of Example 1: 100 mg
(B) Compound of Example 3: 50 mg
(C) Compound of Example 5: 40 mg
  Sulphamethoxazole: 400 mg
  Trimethoprim: 80 ng (ii) An animal food containing the following active ingredients is prepared.
  Compound of Example 6: 200 ppm
  Sulphamethoxazole: 20 ppm
  Trimethoprim: 20 ppm

What is claimed is:

1. A compound of formula (XVIII)

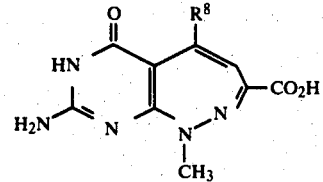

(XVIII)

a tautomer or a salt thereof wherein $R^8$ is lower alkyl, pyridyl, phenyl or phenyl substituted by one or more hydroxy or lower alkoxy.

2. The compound of claim 1 in which $R^8$ is $C_6H_5$.

3. The compound of claim 1 in which $R^8$ is hydroxyl phenyl.

4. The compound of claim 1 in which $R^8$ is $C_6H_2(OCH_3)_3$ where $OCH_3$ is at the 3, 4, 5 position.

5. The compound of claim 1 in which $R^8$ is $CH_3$.

6. The compound of claim 1 in which $R^8$ is 3-pyridyl.

* * * * *